(12) United States Patent
Murthy et al.

(10) Patent No.: US 6,436,956 B1
(45) Date of Patent: *Aug. 20, 2002

(54) USEFUL FORM OF ANHYDROUS PAROXETINE HYDROCHLORIDE

(75) Inventors: K. S. Keshava Murthy; Allan Rey; Gamini Weeratunga, all of Brantford (CA)

(73) Assignee: Brantford Chemicals Inc., Brantford (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/997,697

(22) Filed: Nov. 24, 1997

(30) Foreign Application Priority Data

Dec. 24, 1996 (CA) ............................................... 2193939

(51) Int. Cl.⁷ ..................... A61K 31/445; C07D 405/12
(52) U.S. Cl. ........................................ 514/321; 546/197
(58) Field of Search ........................... 546/197; 514/321

(56) References Cited

U.S. PATENT DOCUMENTS

| | | | | |
|---|---|---|---|---|
| 4,721,723 A | * | 1/1988 | Barnes et al. ................ | 514/321 |
| 4,745,122 A | * | 5/1988 | Lassen ........................ | 514/321 |
| 4,804,669 A | * | 2/1989 | Lassen ........................ | 514/326 |
| 5,672,612 A | * | 9/1997 | Rosen et al. ................ | 514/338 |
| 5,872,132 A | * | 2/1999 | Ward ........................... | 514/321 |

FOREIGN PATENT DOCUMENTS

| | | | |
|---|---|---|---|
| CA | 1287060 | | 7/1991 |
| CA | 2168829 | * | 8/1996 |
| CA | 2187128 | | 6/1997 |
| EP | 810224 | * | 3/1997 |
| WO | 97/34602 | * | 9/1997 |

OTHER PUBLICATIONS

Lynch et al. "Infrared spectroscopic studies . . . " anal. Proce. v.25, pp. 305–306, 1988.*

Lieberman "Pharmaceutical dosage forms" Marcel Dekker, v.2, p. 463, 1989.*

Evans "An introduction to Crystal chemistry" Cambridge press, pp.393–396, 1964.*

Fox et al. "Physics and chemistry of the organic solid state" Intersci. Publ. p.181–182, 1963.*

Buxton, P.C., Lynch, I.R., Roe, J.M., Solid–state forms of paroxetine hydrochloride *International Journal of Pharmaceutics,* 42 (1988), pp. 135–143.

Lynch, I.R., Buxton, P.C., Roe, J.M. Infrared Spectroscopic Studies on the Solid State Forms of Paroxetin Hydrochloride *Analytical Proceedings,* 25 (1988), pp. 305–306.

* cited by examiner

*Primary Examiner*—Ceila Chang
(74) *Attorney, Agent, or Firm*—Marcelo K. Sarkis; Ivor M. Hughes; Neil H. Hughes

(57) ABSTRACT

Paroxetine hydrochloride anhydrous designated as Form IV having at least one, some or all of the following characteristics:

a) Infrared spectra as shown in FIG. 1 and 2, b) A X-ray powder diffraction pattern as shown in Schedule "C", c) A melting point of between about 80°0 C. to about 95° C.

6 Claims, 3 Drawing Sheets

Form IV Paroxetine.HCl - IR Spectrum - KBr

| Peak Y | Name |
|---|---|
| 58.710480 | 612 |
| 52.857971 | 762 |
| 44.374847 | 779 |
| 32.039642 | 830 |
| 43.056488 | 927 |
| 29.637146 | 1036 |
| 42.153931 | 1092 |
| 38.525391 | 1134 |
| 36.847687 | 1160 |
| 16.141510 | 1185 |
| 30.658722 | 1223 |
| 47.321319 | 1269 |
| 61.842346 | 1339 |
| 52.545929 | 1390 |
| 25.639343 | 1470 |
| 16.413116 | 1488 |
| 16.619110 | 1511 |
| 44.905090 | 1605 |
| 50.696564 | 1631 |
| 34.636688 | 2769 |
| 33.396912 | 2927 |
| 56.149292 | 3424 |

Form IV Paroxetine.HCl - IR Spectrum - Nujol

```
threshold    2.00%; band
  cm-1      %        cm-1      %        cm-1      %        cm-1      %
 3413.8   56.07     2922.0    5.47     2853.2    7.09     2515.1   36.01
 1631.4   45.27     1604.1   37.40     1510.5   16.99     1487.4   14.83
 1466.8   11.28     1378.2   33.14     1340.7   47.65     1269.5   36.92
 1223.4   22.69     1183.9   14.72     1160.5   27.74     1135.1   28.50
 1092.9   31.84     1073.0   42.76     1035.7   22.06      928.3   32.84
  830.7   24.21      798.3   38.65      780.1   36.16      762.5   45.13
  720.8   49.67      573.9   26.22
26 peaks found
```

USEFUL FORM OF ANHYDROUS PAROXETINE HYDROCHLORIDE

FIELD OF INVENTION

This invention relates to a new and useful form of paroxetine hydrochloride (anhydrous) and its preparation thereof.

BACKGROUND OF THE INVENTION

Canadian Letter Patent 1,287,060 describes two distinct forms of paroxetine hydrochloride viz., an anhydrous form of paroxetine hydrochloride and the hemihydrate form of paroxetine hydrochloride (paroxetine hydrochloride_$H_2O$). The existence of these forms is confirmed in the International Journal of Pharmaceutics, 42, pp. 135–143 and Analytical Proceedings, 25, pp. 305–306, both published in 1988. Canadian Patent Applications Serial No. 2,168,829 (1996) and 2,187,128 (Brantford Chemicals Inc.) (1996) purport to describe several new polymorphs of paroxetine hydrochloride anhydrate.

The two forms described in Canadian Letter Patent 1,287,060, International Journal of Pharmaceutics, 42, pp. 135–143 (1988), and Analytical Proceedings, 25, pp. 305–306 (1988) have been known for a substantial period of time, particularly the anhydrous form, which has a melting point of about 118° C. and which is known to be hygroscopic making this material difficult to handle. Coupled with this is the fact that the said anhydrous material is also light and fluffy, which further compounds the problems of handling (filtration and drying) and formulating the active into the final dosage form.

The hemihydrate form is purportedly stable. The purpose of the hemihydrate is to provide material which is less hygroscopic, however the compound does include additional amounts of water. If a suitable form of paroxetine hydrochloride anhydrate was available, it should be easily handled with minimal difficulties with respect to the hygroscopic nature of the material and should not be light and fluffy. Preferably the paroxetine hydrochloride anhydrous would be in a form having a dense structure which enables the raw active to be easily formulated into final dosage form. Such dense material should, of course, also be readily dried and any residual solvents easily removed to yield the bulk active and should be readily adapted for use in the commercial manufacture of anhydrous paroxetine hydrochloride, the active ingredient in the final formulation.

It is therefore an object of this invention to provide such improved paroxetine hydrochloride anhydrous which overcomes the disadvantages of the prior forms of the raw active which suffers from the above deficiencies, particularly the hygroscopic nature of the paroxetine hydrochloride anhydrate, the light fluffy nature of the some forms of paroxetine hydrochloride anhydrate, and the other deficiencies which would deter one from using paroxetine hydrochloride anhydrous and require such person to use the paroxetine hydrochloride hemihydrate in its place.

Further and other objects of the invention will be realized by those skilled in the art from the following summary of the invention and detailed description of examples thereof.

SUMMARY OF THE INVENTION

In our research and the research of others, it has been determined that paroxetine hydrochloride anhydrous may exist in a number of polymorphic forms. Our research unexpectedly revealed to us a new amorphous form of paroxetine hydrochloride anhydrous which was very dense, having a bulk density exceeding about 0.6 g/mL and a tapped density exceeding about 0.9 g/mL and which is substantially non-hygroscopic. We have identified this Form as Form IV. Form IV did not retain, we discovered, residual solvent in excess of about 0.1%, even leaving the material exposed to open air for a period of three days (ca. 50% relative humidity), Form IV did not take on moisture more than 1.5% by weight. Form IV, as well, was very stable and was distinguished from the other forms previously described by a melting point between about 81–85° C. Furthermore, the conversion of Form IV to the hemihydrate polymorph, as indicated by a differential scanning calorimetry (DSC) maximum of 143° C., occurs at a negligible rate even in humid environments. Form IV has the capability of being formulated into final dosage form and is easily manufactured in commercial quantities by processes described in the examples herein.

DETAILED DESCRIPTION

Example 1 for making Paroxetine Hydrochloride Anhydrate of the $P_{119}$ Polymorph Paroxetine hydrochloride (209.8 g) is placed in a 2-L three-necked flask equipped with a mechanical stirrer, reflux condenser, and thermometer followed by 2-propanol (anhydrous, 1.7 L). This flask is heated under nitrogen to dissolution (internal temperature=83° C.), and subsequently cooled to 22° C. (ca. 4 hours). The flask is cooled to 10° C. and stirred a further 1 hour at which point the precipitate is isolated by Buchner filtration. The filter cake is rinsed with 210 mL of 2-propanol and transferred to a drying oven and dried in vacuo at 50° C. for 36 hours. This afforded 207.5-g of anhydrous paroxetine hydrochloride having a melting point of 116.8–117.9° C. The material contained a small amount of residual 2-propanol.

Example 2 for making Form IV

Figure 1:
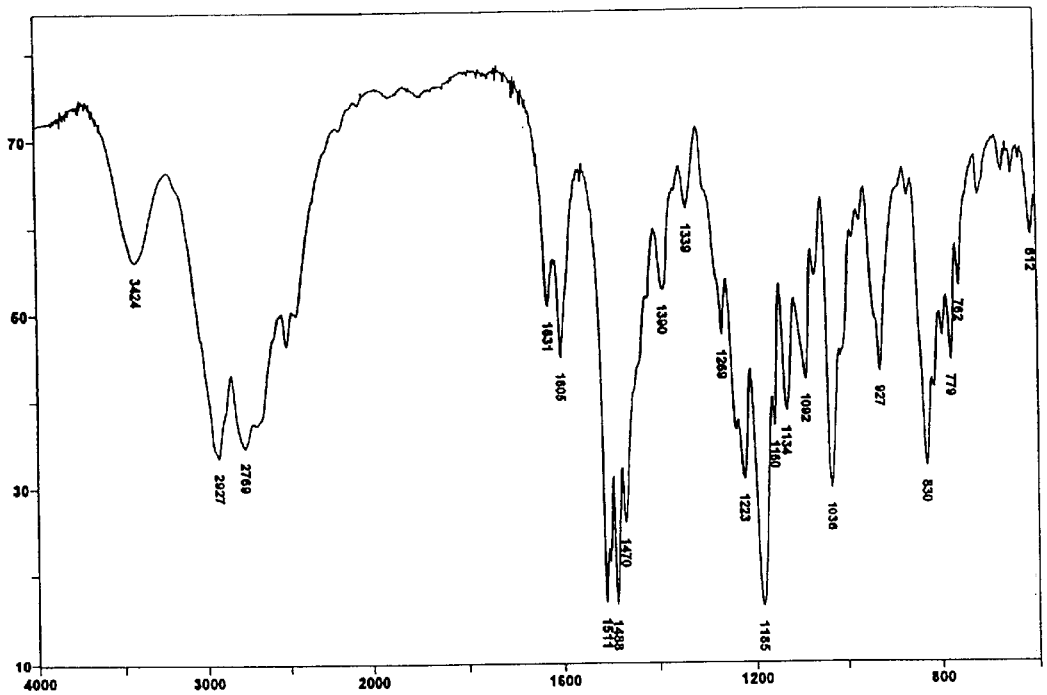
FIG. 1 is the infrared spectrum of Form IV in KBr.
Figure 2:
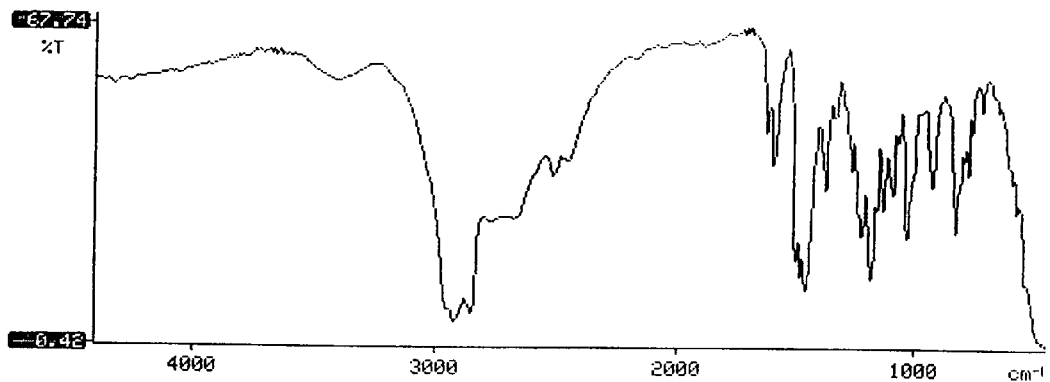
FIG. 2 is the infrared spectrum of Form IV in Nujol.
Figure 3:
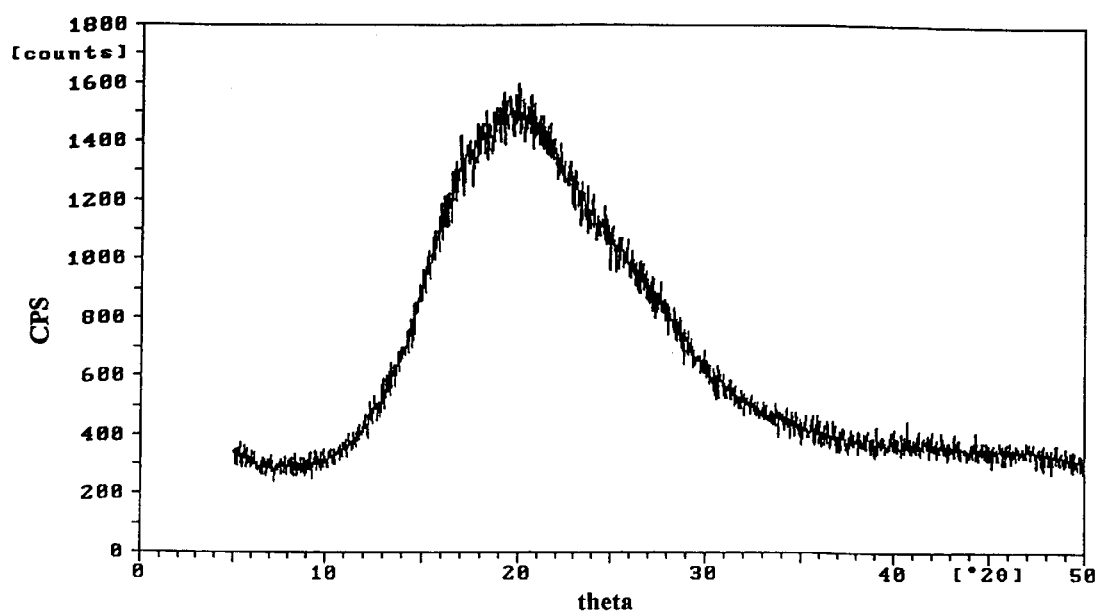
FIG. 3 is the X-ray powder diffraction patterns of Form IV.

The anhydrous paroxetine hydrochloride (60 g) from Example 1 is placed in a 250 mL, two-necked round bottom flask equipped with a vacuum adapter and mechanical stirrer. This flask is placed in an oil bath and is stirred and heated under vacuum (ca. 20 mmHg) to the point at which the solid becomes a viscous oil (ca. 155° C. external temperature). After the paroxetine hydrochloride melts, stirring is continued for 10 min. whereupon the flask is removed from the oil-bath and cooled to 20–25° C. The glass-like paroxetine hydrochloride is pulverized using a mortar and pestle, or milled, and stored in a dry atmosphere. This provided an essentially quantitative recovery of paroxetine hydrochloride (anhydrous) of Form IV. The melting point range was 81–85° C. The infrared spectra (KBr and Nujol), and X-ray powder diffractogram are shown in FIGS. 1, 2 and 3, respectively and labelled as Form IV.

Example 3 for making Form IV

Solid paroxetine hydrochloride (30 g) is placed in a 100 mL, two-necked round bottom flask equipped with a mechanical stirrer and nitrogen inlet and outlet lines. This flask is placed in an oil bath and is stirred and heated under vacuum (ca. 20 mmHg) to the point at which the solid becomes a viscous oil (ca. 155° C. external temperature). After the paroxetine hydrochloride melts, stirring is continued for 10 min. whereupon the flask is removed from the oil-bath and cooled to 20–25° C. The glass-like paroxetine hydrochloride is pulverized using a mortar and pestle, or milled, and stored in a dry atmosphere. This provided an essentially quantitative recovery of paroxetine hydrochloride (anhydrous) of Form IV.

Example 4 for making Form IV

Solid paroxetine hydrochloride (10 g) is placed in a 100 mL, three-necked round bottom flask equipped with a mechanical stirrer and nitrogen inlet and outlet lines. This flask is placed in an oil bath and is stirred and heated under a stream of nitrogen to the point at which the solid becomes a viscous oil (ca. 155° C. external temperature). After the paroxetine hydrochloride melts, stirring is continued for 10 min. whereupon the flask is removed from the oil-bath and cooled to 20–25° C. The glass-like paroxetine hydrochloride is pulverized using a mortar and pestle, or milled, and stored in a dry atmosphere. This provided an essentially quantitative recovery of paroxetine hydrochloride (anhydrous) of Form IV.

Example 5 for making Form IV

The anhydrous paroxetine hydrochloride (50 g) obtained by the 2-propanol recrystallization procedure described in example 1 is placed in a 500 mL, single-necked round bottom flask. To this flask is added methanol (100 mL) and the contents are stirred until complete dissolution (ca. 5 minutes). The methanol is then removed using rotary evaporation (bath temperature=30° C.) until a foam forms. The sample is dried further in vacuo (20 mmHg) at 20° C. for 2 days. The anhydrous paroxetine hydrochloride is pulverized and stored in a dry atmosphere. This provided a quantitative recovery of paroxetine hydrochloride anhydrate of Form IV. This material had slightly lower bulk and tapped densities (exceeding 0.43 g/mL and 0.58 g/mL, respectively) compared to the material of Example 2.

The embodiments of this invention in which an exclusive property or privilege is claimed are as follows:

1. Amorphous paroxetine hydrochloride anhydrous in Form IV having at least one, some or all of the following characteristics:

(a) Infrared spectra according to FIGS. 1 and 2:

(b) A X-ray powder diffraction pattern according to FIG. 3:

(c) A melting point of between about 80° C. to about 95° C.; and wherein said amorphous paroxetine hydrochloride anhydrous retains a residual solvent less than about 0.1%.

2. Amorphous paroxetine hydrochloride anhydrous in Form IV having infrared spectra according to FIGS. 1 and 2:

and wherein said amorphous paroxetine hydrochloride anhydrous retains a residual solvent less than about 0.1%.

3. Amorphous Paroxetine hydrochloride anhydrous in Form IV having the following X-ray powder diffraction pattern according to FIG. 3:

and wherein said amorphous paroxetine hydrochloride anhydrous retains a residual solvent less than about 0.1%.

4. Amorphous paroxetine hydrochloride anhydrous in Form IV having a melting point of between about 80° C. to about 95° C. and wherein said amorphous paroxetine hydrochloride anhydrous retains a residual solvent less than about 0.1%.

5. A method of treating depression in a patient in need thereof comprising administering to a patient an effective antidepressant amount of amorphous paroxetine hydrochloride anhydrous in Form IV of claim 1 and wherein said amorphous paroxetine hydrochloride anhydrous retains a residual solvent less than about 0.1%.

6. The Amorphous paroxetine hydrochloride anhydrous in Form IV of claim 4 wherein its melting point is between about 81° C. and about 85° C.

* * * * *